United States Patent
Martin et al.

(10) Patent No.: US 10,144,916 B2
(45) Date of Patent: Dec. 4, 2018

(54) CELL SURFACE SIGNATURE FOR PROCESSING CARDIOMYOCYTE SUBSETS FROM HETEROGENEOUS CELL SAMPLES

(71) Applicant: Becton, Dickinson and Company, Franklin Lakes, NJ (US)

(72) Inventors: Jody Martin, Encinitas, CA (US); Jason G. Vidal, Oceanside, CA (US); Christian T. Carson, Del Mar, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 102 days.

(21) Appl. No.: 15/304,830

(22) PCT Filed: May 8, 2015

(86) PCT No.: PCT/US2015/029913
§ 371 (c)(1),
(2) Date: Oct. 17, 2016

(87) PCT Pub. No.: WO2015/172037
PCT Pub. Date: Nov. 12, 2015

(65) Prior Publication Data
US 2017/0153236 A1 Jun. 1, 2017

Related U.S. Application Data

(60) Provisional application No. 61/991,192, filed on May 9, 2014.

(51) Int. Cl.
*C12N 5/077* (2010.01)
*G01N 33/569* (2006.01)

(52) U.S. Cl.
CPC ..... *C12N 5/0657* (2013.01); *G01N 33/56966* (2013.01); *G01N 2333/70596* (2013.01)

(58) Field of Classification Search
CPC ... G01N 33/56966; G01N 2333/70596; C12N 5/0657
See application file for complete search history.

(56) References Cited

U.S. PATENT DOCUMENTS

| 2012/0009158 A1* | 1/2012 | Chien | A61K 35/34 424/93.7 |
| 2012/0301445 A1 | 11/2012 | Blanpain et al. | |
| 2013/0230921 A1* | 9/2013 | Keller | C12N 5/0657 435/366 |

FOREIGN PATENT DOCUMENTS

EP  2 875 819 A1 * 11/2013  ............. A61K 35/34

OTHER PUBLICATIONS

Xu Differentiation and enrichment of cardiomyocytes from human pluripotent cells. Journal of Molecular and Cellular Cardiology. 52: 1203-1212 (2012).*

(Continued)

*Primary Examiner* — Gailene Gabel
(74) *Attorney, Agent, or Firm* — Kathleen Y. Rao; Bret E. Field; Bozicevic, Field & Francis LLP

(57) ABSTRACT

Methods are provided for distinguishing a cardiomyocyte subset in a heterogeneous cellular sample. Aspects of the methods include contacting the heterogeneous cellular sample with a cell surface marker specific binding member, and then distinguishing a cardiomyocyte subset of the cellular sample based on binding to the cell surface marker specific binding member. Also provided are devices, compositions and kits that find use in performing the subject methods.

13 Claims, 8 Drawing Sheets

(56) References Cited

OTHER PUBLICATIONS

Dubois et al. SIRPA is a specific cell-surface marker for isolating cardiomyocytes derived from human pluripotent stem cells. Nature Biotechnology 29 (11): 1011-1018 (Nov. 2011).*
Meng et al. Induced pluripotent stem cells derived from mouse models of lysosomal storage disorders. PNAS 107 (17) 7886-7891 (Apr. 27, 2010).*
Aerts et al. Elevated globotriaosylsphingosine is a hallmark of Fabry disease. PNAS 105 (8): 2812-2817 (Feb. 26, 2008).*
Dubois, et al. "SIRPA is a specific cell-surface marker for isolating cardiomyocytes derived from human pluripotent stem cells", Nat Biotechnol. ; 29(11): 1011-1018, Jul. 18 , 2016.
Meng, et al. "Induced pluripotent stem cells derived from mouse models of lysosomal storage disorders", Proc Natl Acad Sci U S A. Apr. 27, 2010;107(17):7886-91.
Uosaki, et al. "Efficient and scalable purification of cardiomyocytes from human embryonic and induced pluripotent stem cells by VCAM1 surface expression", PLoS One. 2011;6(8):e23657.
Xu "Differentiation and enrichment of cardiomyocytes from human pluripotent stem cells" J Mol Cell Cardiol. Jun. 2012;52(6):1203-12.

* cited by examiner

CELL SURFACE SIGNATURE FOR PROCESSING CARDIOMYOCYTE SUBSETS FROM HETEROGENEOUS CELL SAMPLES

CROSS-REFERENCE TO RELATED APPLICATIONS

Pursuant to 35 U.S.C. § 119 (e), this application claims priority to the filing date of U.S. Provisional Patent Application Ser. No. 61/991,192 filed May 9, 2014, the disclosure of which application is herein incorporated by reference.

INTRODUCTION

Cardiovascular disease encompasses a wide variety of conditions, including cardiomyopathy, heart failure, congenital heart disease, cardiac dysrhythmias, inflammatory heart disease, valvular heart disease, ventricular tachycardia and atrial fibrillation in addition to coronary artery disease (causing heart attack). Taken together, these cardiovascular diseases are the leading cause of death in the US and a major cause of death worldwide. As such, development of drug-based and cell-based therapies for various cardiovascular diseases is a primary research focus worldwide.

Cardiomyocytes derived from pluripotent stem cells have been used to model heart disease, facilitate small molecule testing, and provide cellular based therapies. Characterization of cardiomyocytes derived from pluripotent stem cells enables optimization of cardiomyogenesis techniques, and provides insight into basic developmental biology.

SUMMARY

Methods are provided for distinguishing a cardiomyocyte subset in a heterogeneous cellular sample. Aspects of the methods include contacting the heterogeneous cellular sample with a cell surface marker specific binding member, and then distinguishing a cardiomyocyte subset of the cellular sample based on binding or absence of binding to the cell surface marker specific binding member, i.e., whether binding to the cell surface marker occurs. Also provided are devices, compositions and kits that find use in performing the subject methods.

BRIEF DESCRIPTION OF THE FIGURES

FIG. 1A shows gating of live cells by scatter properties. FIG. 1B shows gating of GFP+ cells. FIG. 1C shows expression of CD77 and CD200. FIG. 1D shows gating of $CD77^{bright}$ and $CD200^{neg}$ cells. FIG. 1E shows expression of GFP.

FIG. 2A shows gating of cells by scatter properties. FIG. 2B shows gating of $CD77^{bright}$ and $CD200^{neg}$ cells. FIG. 2C shows expression of GFP and cTnI. FIG. 2D shows gating of GFP+ and $cTnI^{high}$ cells. FIG. 2E shows expression of CD77.

FIG. 4A provides scatter plots showing the expression of CD77, CD29, CD340 and CD172a (SIRPA) with GFP. FIG. 4B provides scatter plots showing co-expression of CD172a, CD340 and CD29 with CD77. GFP+ cell events, gated as shown in FIG. 1B, are colored green.

FIG. 5A provides scatter plots showing the gating of live singlets (single cells in suspension). FIG. 5B provides scatter plots showing the expression of CD172a, cTnI, and CD77.

DETAILED DESCRIPTION

Figure 1:
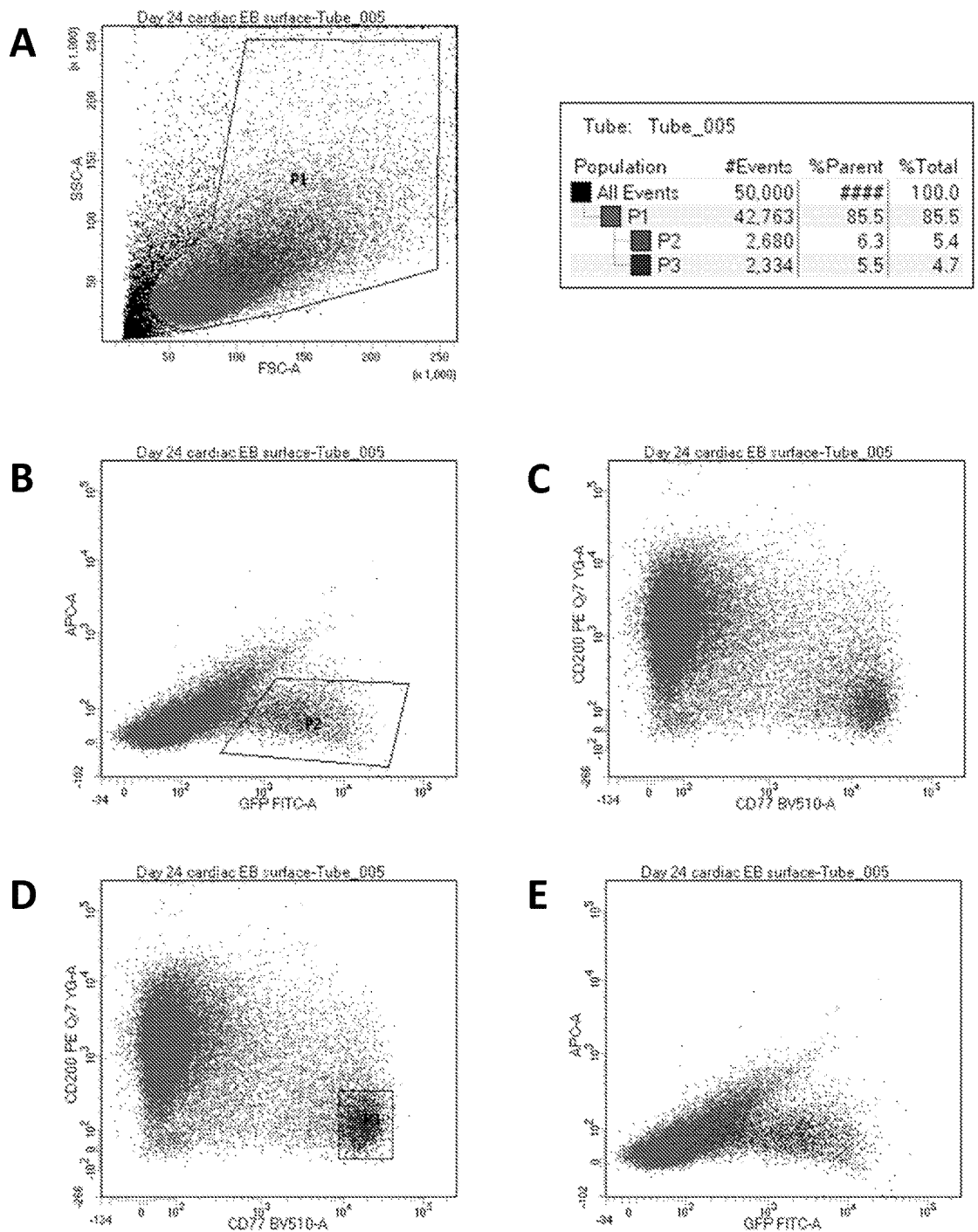
FIGS. 1A-E provide scatter plots showing the gating and analysis of an H9 cell line expressing GFP from the MLC2V promoter, differentiated for 25 days by embryoid body culture.

Methods are provided for distinguishing a cardiomyocyte subset in a heterogeneous cellular sample. Aspects of the methods include contacting the heterogeneous cellular sample with a cell surface marker specific binding member, and then distinguishing a cardiomyocyte subset of the cellular sample based on binding to the cell surface marker specific binding member. Also provided are devices, compositions and kits that find use in performing the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing embodiments of the invention, aspects of embodiments of the methods will be described first in greater detail. Next, embodiments of systems and kits that may be used in practicing methods of the invention are reviewed.

Methods

As summarized above, aspects of the invention include distinguishing a cardiomyocyte subset of a heterogeneous cellular sample. By distinguishing a cardiomyocyte subset is meant processing a cardiomyocyte subset in a manner that is different from other cellular constituents of the heterogeneous cellular sample. Distinguishing the cardiomyocyte subset of interest may include a variety of different protocols by which the cardiomyocyte subset is processed. For example, in some instances the distinguishing may include separating the cardiomyocyte subset of interest from other cells in the heterogeneous cellular sample. In some instances, the distinguishing may include enriching heterogeneous cellular sample for the cardiomyocyte subset of interest (e.g., by depleting or removing other cells). In some instances, the distinguishing may include identifying the cardiomyocyte subset of interest. In some instances, the distinguishing may include providing an assessment of the cardiomyocyte subset of interest (e.g., based on one or more characteristics of the cardiomyocyte subset). Further details regarding types of distinguishing are provided below.

The term "cardiomyocyte" is employed in its conventional sense to refer to cardiac muscle cells (i.e., myocardiocytes or cardiac myocytes). Cardiomyocytes are the muscle cells (myocytes) that make up the cardiac muscle, where each myocardial cell contains myofibrils. Cardiomyocytes show striations similar to those on skeletal muscle cells, but unlike multinucleated skeletal cells, may contain only one nucleus or 2 or 3 nuclei. Cardiomyocytes have a high mitochondrial density, which allows them to produce adenosine triphosphate (ATP) quickly, making them highly resistant to fatigue.

Cariomyocyte subsets of interest are subpopulations or types of cardiomyocytes. Cardiomyocyte subsets of interest include ventricular cardiomyocytes and atrial cardiomyocytes. Ventricular cardiomyocytes are cardiomyocytes that are found in the ventricle chambers of the heart, which are the heart chambers from which blood is pumped out of or away from the heart, e.g., to the body or lungs. Atrial cardiomyocytes are cardiomyocytes that are found in the atrial chambers of the heart, which are the heart chambers from which blood is collected and pumped into the ventricles, e.g., from the body or lungs.

As detailed below, aspects of the methods include contacting a heterogeneous cellular sample with a cell surface marker specific binding member and then distinguishing a cardiomyocyte subset of interest, e.g., ventricular or atrial cardiomyocyte subset, based on binding or absence of binding to the cell surface marker specific binding member, i.e., based on whether the binding member binds to the cell surface marker. In certain aspects, the distinguishing is performed based on the binding of one or more specific binding members. For example, distinguishing may include isolating or depleting cells bound to one or more specific binding members to separate or enrich for the cardiomyocyte subset. Alternatively or in addition, distinguishing may include identifying the cardiomyocyte subset based on one or more specific binding members bound to cells in the sample (e.g., as measured by one or more signals provided by the one or more binding members). In certain aspects, identifying the cardiomyocyte subset may enable enrichment, separation and/or assessment of the cardiomyocyte subset. For example, distinguishing may include identifying the cardiomyocyte subset and may further include providing an assessment based on a characteristic of the identified cardiomyocyte subset, such as number (relative or total), additional specific binding members bound to cells of the identified cardiomyocyte subset, and so forth. Steps of distinguishing are described in further detail below.

Heterogeneous Cellular Sample

The heterogeneous cellular sample may include mammalian cells (e.g., human, non-human primate, murine, etc.). In certain aspects, the sample may include myocytes, such as cardiomyocytes (e.g., atrial cardiomyocytes, ventricular cardiomyocytes, or a precursor thereof). In addition, the sample may include human pluripotent stem cells (hPSCs), such as embryonic stem cells (ESCs), induced pluripotent stem cells (iPSCs), or a combination thereof. Alternatively or in addition, the sample may include feeder cells, such as fibroblasts. In certain aspects, the cellular sample may be of a cardiac differentiation culture, induced cardiac culture (e.g., from fibroblasts), embryoid body culture, primary cell isolate, or any suitable culture from which cardiomyocytes may be derived.

In certain embodiments, the method may include steps of obtaining and/or culturing the cell sample prior to the step of contacting. For example, the method may include obtaining cells from umbilical cord tissue, an embryo, or from a subject's blood, bone marrow, skin, heart, liver, stomach, and so forth. Cells obtained from any of the above sources may be further purified (e.g., enriched) based on morphology, surface marker expression and/or by continued passage. Alternatively, the cellular sample may include immortalized cells, such as the H9 human ESC line, the HES2 cell line, or any other suitable cell line.

For isolation of cells from tissue, an appropriate solution may be used for dispersion or suspension. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. The separated cells may be collected in any appropriate medium that maintains the viability of the cells. Various media/buffers are commercially available and may be used according to the nature of the cells, including dMEM, HBSS, dPBS, RPMI, Iscove's medium, etc., frequently supplemented with fetal calf serum or human platelet lysate.

The obtained cells may then be cultured under conditions suitable for production and/or expansion. The culture conditions may include one or more passages and in some instances ten or fewer passages. The culture conditions may include one or more factors for maintaining multipotency in cells. Examples of such factors include fetal bovine serum (FBS), fibroblast growth factor, human platelet lysate, vectors for transfecting genes (such as Oct4, Sox2, cMyc, and Klf4) for inducing/maintaining pluripotency, etc. The cellular culture may be frozen (e.g., in 5% or greater DMSO and at liquid nitrogen temperatures) prior to use, as desired.

The methods may include obtaining cells and optionally culturing cells under conditions suitable to derive, for example, cardiomyocytes (e.g., ventricular and/or atrial cardiomyocytes). For example, stem cells may be cultured to form embryoid bodies (e.g., by culturing in suspension, in round bottom wells, or in droplets suspended from the top of a cell culture flask or multiwall plate). Alternatively, stem cells may be cultured as a monolayer (e.g., with or without a feeder layer). Certain reagents, such as fetal calf serum and human platelet lysate may be added to the culture for all or part of the time period over which cardiomyocytes are derived. In addition, factors such as retinoic acid, fibroblast growth factor (FGF), activin A, bone morphogenic factor (BMP4), VEGF, Dickkopf-1 (DKK-1), exogenous glucose, leukemia inhibitory factor, ROS species, Verapamil, cyclosporine, 5-Aza-2'-deoxycytidine, ascorbic acid or a combination thereof may be added to the cell culture to further induce cardiomyocyte differentiation. Methods of obtaining cardiomyocytes from stem cells are discussed by Chan. et al., "Fibroblast Growth Factor-10 Promotes Cardiomyocyte Differentiation from Embryonic and Induced Pluripotent Stem Cells" (*PLoS One*. 2010; 5(12): e14414) and in Becker et al., "Inducing Embryonic Stem Cells to Become Cardiomyocytes." (*Stem Cell Biology and Regenerative Medicine*. 2011; p. 7-24), where such methods may be employed in embodiments of the invention.

In certain embodiments, the cells in the sample may be live, such as when isolation of cells is desired. In other embodiments, cells of the sample may be dead (e.g., fixed and/or permeabilized for assessment of, for example, intracellular markers by fluorescence microscopy or flow cytometry), such as when only identification and/or characterization is desired.

In certain aspects, the methods may include fixing the sample, for example, before contacting the sample with one or more specific binding members. The cells of the sample may be fixed through exposure to any of a number of cell fixing agents (i.e., fixation reagents), such as paraformaldehyde, glutaraldehyde, methanol, acetone, formalin, or any combination thereof. Other fixatives and fixation methods may be employed, as desired. Fixation time may vary, and in some instances ranges from 1 minute and 1 hour, such as 5 minutes and 30 minutes. The temperature at which fixation takes place may vary, and in some instances the temperature ranges from −30° C. to 40° C.

In certain aspects, the sample may be treated with a permeabilization agent prior to contacting the sample with an intracellular marker specific binding member. Permeabilization may allow an intracellular marker specific binding member to enter cells in the sample. Permeabilization may take place before, after, or at the same time as the fixation previously described. The cells of the sample may be permeabilized through exposure to any of a number of cell permeabilizing agents, such as methanol, acetone or a detergent (e.g., triton, NP-40, saponin, tween 20, digitonin, leucoperm, etc.), or a combination thereof. Permeabilization time may vary, and in some instances ranges from 1 minute to 1 hour, such as from 5 minutes to 30 minutes. The temperature at which permeabilization takes place may vary, and in some instances the temperature may range from 0° C. to 50° C. In certain aspects, the cells in the cellular sample are not permeabilized prior to when the sample is contacted with the cell surface marker specific binding member.

Contacting the Heterogeneous Cellular Sample with a Cell Surface Specific Binding Member(s)

Aspects of the invention include samples of the above embodiments contacted with one or more specific binding members (e.g., as described below). As summarized above, the method includes contacting a heterogeneous cellular sample with a cell surface marker specific binding member. The cell surface marker specific binding member may be a ventricular cardiomyocyte cell surface specific binding member. In certain aspects, the ventricular cardiomyocyte cell surface specific binding member may be a CD77 specific binding member. CD77 is a ganglioside and is also known as Globotriaosylceramide or Gb3. Further details regarding CD77 are available at the website produced by placing "http://www" before ".nlm.nih.gov/cgi/mesh/2011/MB_cgi?mode=&term=globotriaosylceramide"; and are reported in Bekri et al., "The role of ceramide trihexoside (globotriaosylceramide) in the diagnosis and follow-up of the efficacy of treatment of Fabry disease: a review of the literature" Cardiovasc. Hematol. Agents. Med. Chem. (October, 2006) 4 (4): 289-97.

The method may further include contacting the sample with one or more non-cardiomyocyte specific binding members. The one or more non-cardiomyocyte specific binding members may specifically bind one or more cell surface markers expressed by one or more non-cardiomyocyte cell populations, such as a stem cell population (e.g., embryonic stem cells (ESCs), induced pluripotent stem cells (iPSCs), hematopoietic stem cells, fibroblasts, myoblasts and so forth). In certain aspects, one or more of the non-cardiomyocyte specific binding members may be specific for one or more of CD90, CD140b, CD200, CD13, CD31, CD144, CD49a, CD167b and TRA-1-60. Other non-cardiomyocyte specific binding members may include any surface markers expressed by non-cardiomyocytes in the cellular sample. In certain aspects, the method may include contacting the sample with multiple non-cardiomyocyte specific binding members. For example, the one or more non-cardiomyocyte specific binding members may be specific for CD90, CD140b, and CD200. In addition or alternatively, the method may include contacting the sample with a cardiomyocyte specific binding member. In certain aspects, the cardiomyocyte specific binding member may be specific for one of CD172a, CD340, CD43 and CD29. For example, the cardiomyocyte specific binding member may be specific for CD172a. In certain aspects, the method may include contacting the sample with multiple cardiomyocyte specific binding members.

A variety of specific binding members are suitable for embodiments of the subject invention. In any of the above embodiments, one or more of the specific binding members (e.g., a ventricular specific binding member, non-cardiomyocyte specific binding member, cardiomyocyte specific binding member, intracellular marker specific binding member) may include a specific binding domain. In certain aspects, the specific binding domain may be an antibody or a fragment thereof. The specific binding member may also include a processing domain, such as a solid support or a detectable label, e.g., as described in greater detail below. In some instances the specific binding member is a non-naturally occurring specific binding member. For example, the specific binding member may include a processing domain, such as described below, that is not naturally present in a specific binding member, such as a naturally occurring antibody. In some instances, the specific binding member may be part of a specific binding member composition that is not naturally occurring, e.g., a composition in which there is only a single type of the specific binding member in multiple copies (e.g., monoclonal antibody composition), a composition in which the specific binding member is present in a non-naturally occurring medium, such as a buffered medium that lacks one or more components found in the naturally occurring medium (e.g., blood) of the specific binding member (for example, the specific binding member may be present in a composition that lacks cellular components or blood proteins), etc.

In certain embodiments, a specific binding member may include a specific binding domain. The terms "specific binding", "specific for", "specifically binds" and the like, refer to the preferential binding of a the binding member to a particular target (e.g., to a cell type, to a specific extracellular or intracellular marker, etc.). The specific binding domain may bind (e.g., covalently or non-covalently) to a specific epitope on or within the cell. In certain aspects, a specific binding domain non-covalently binds to a target. In such instances, the specific binding domain association with the binding target (e.g., CD77) may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. A variety of different types of specific binding domains may be employed. Specific binding domains of interest include, but are not limited to, antibodies, proteins, peptides, haptens, nucleic acids, etc. The term "antibody" as used herein includes polyclonal or monoclonal antibodies or fragments that are sufficient to bind to a target of interest. The term "antibody" also includes antibody fragments, such as, monomeric Fab fragments, monomeric Fab' fragments, or dimeric F(ab)'2 fragments. Also within the scope of the term "antibody" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

As mentioned above, one or more specific binding members of the subject embodiments may include (or be conjugated to) a processing domain. By processing domain is meant any suitable domain (e.g., molecule, structure, etc.) for identifying the presence of the specific binding member (such as a label domain), separating cells bound by the specific binding member (such as a solid support), or both.

In certain aspects, separation or enrichment, e.g., as described below, may be performed using specific binding members that are conjugated to a solid support. The solid support may be any suitable solid support, such as the interior surface of a container (e.g., flask, tube, well, etc.) or a microparticle. For example, the solid support may be a magnetic microparticle, and separation may include magnetically separating or removing cells bound to the microparticle from unbound cells.

In certain embodiments, the processing domain may be a label domain. For example, the specific binding member may be detectably labeled with a fluorophore. The label domain may be a colored dye, a phosphorescent label, a fluorescent label, a mass tag, a radioactive label, or any other suitable label. For example, the label domain may be a fluorescent label detectible based on, for example, fluorescence emission maxima, fluorescence polarization, fluorescence lifetime, light scatter, or a combination thereof. In certain aspects, the label domain may be a fluorophore (i.e., a fluorescent label, fluorescent dye, etc.). Fluorophores can be selected from any of the many dyes suitable for use in analytical applications (e.g., flow cytometry, imaging, etc.). A large number of dyes are commercially available from a variety of sources, such as, for example, Molecular Probes (Eugene, Oreg.) and Exciton (Dayton, Ohio). Examples of fluorophores that may be incorporated into the microparticles include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl) aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio). The fluorescent label may be distinguishable based on fluorescence emission maxima, and optionally further based on light scatter or extinction.

In other aspects, the label domain may be a metal isotope detectible by mass spectroscopy, such as by the time of flight mass spectrometer used in mass cytometery, e.g., as described in international patent application serial no. PCT/

US2012/020950 published as WO/2010/097070, the disclosure of which is herein incorporated by reference.

Cardiomyocyte Subset Distinguishment

As discussed above, aspects of the methods include distinguishing a cardiomyocyte subset in a heterogeneous cellular sample. Distinguishing may include separating, enriching, identifying, providing an assessment, among other protocols in which the target cardiomyocyte subset of interest is treated in a way that is different or distinct from the treatment of other cellular constituents of the heterogeneous cellular sample. In certain aspects, distinguishing may include separating cells based on binding to the surface marker specific binding member. For example, the method may include separating (e.g., isolating) cells bound to a ventricular cardiomyocyte specific binding member (such as a CD77 specific binding member). Alternatively, the method may include separating cells bound to the ventricular cardiomyocyte specific binding member and unbound to one or more non-cardiomyocyte specific binding members. In either of the above examples, the separated cells may include ventricular cardiomyocytes. In yet another example, the method may include separating cells bound to a cardiomyocyte specific binding member and unbound to both a ventricular cardiomyocyte specific binding member (such as a CD77 specific binding member) and one or more non-cardiomyocyte specific binding members. In this example, the separated cells may include atrial cardiomyocytes and/or a common progenitor. Separating refers to apportioning target cells from other constituents of an initial composition from which the cells are separated.

In certain aspects, distinguishing may include enriching for the cardiomyocytes, such as by removing (e.g., depleting) cells bound to one or more non-cardiomyocyte specific binding members. For example, the cell surface marker specific binding member may be a non-cardiomyocyte specific binding member (such as CD90, CD140b, CD13, CD31, CD144, CD49a, CD167b, and/or TRA-1-60 specific binding members), and distinguishing may include enriching for the cardiomyocyte subset by depleting cells bound to one or more non-cardiomyocyte specific binding members. In this example, cells bound to one or more non-cardiomyocyte specific binding members conjugated to magnetic microparticles may be separated by applying a magnetic field to the sample.

Distinguishing may include identifying cells (e.g., based upon a cell surface signature). In certain embodiments, distinguishing may include identifying cells based upon the presence of a signal (e.g., a fluorescence signal as described above) provided by the cell surface specific binding member (e.g., a ventricular cardiomyocyte specific binding member such as a CD77 specific binding member) and optionally one or more signals provided by one or more additional binding members (e.g., a non-cardiomyocyte specific binding member, a cardiomyocyte specific binding member, etc.). In certain aspects, distinguishing may involve identifying cells in the sample which are bound to the ventricular cardiomyocyte specific binding member as ventricular cardiomyocytes, such as when a signal obtained from the ventricular cardiomyocyte specific binding member exceeds a predetermined threshold value. For example, distinguishing may involve identifying cells in the sample which are bound to the ventricular cardiomyocyte specific binding member and bound to one or more ventricular cardiomyocyte specific binding members as ventricular cardiomyocytes. Alternatively or in addition, distinguishing may involve identifying cells in the sample which are unbound to the ventricular cardiomyocyte specific binding member as atrial cardiomyocytes, such as when a signal obtained from the ventricular cardiomyocyte specific binding member is less than a predetermined threshold value. For example, distinguishing may involve identifying cells bound to the cardiomyocyte specific binding member and unbound to both the ventricular cardiomyocyte specific binding member and the non-cardiomyocyte specific binding member as atrial cardiomyocytes (or a cardiomyocyte precursor).

In any of the above embodiments, the threshold value may be determined based upon input from a user or may be based upon a standardized control. In one example, the standardized control may be control particles, such as fluorescent control beads or control cells. The control particles may serve as a positive or negative control. Alternatively or in addition, the threshold value may be determined by an algorithm configured to cluster and/or otherwise separate cell populations based on a signal, such as a signal provided by the ventricular cardiomyocyte specific binding member.

In addition, the distinguishing may include providing an assessment of one or more characteristics of cells identified by any of the above embodiments. For example, the assessment may include a number of the identified cells, or a relative number of the identified cells (e.g., a ratio, percentage, etc., of the identified cells to the number of cells in the sample or number of a subset of cells in the sample). Alternatively or in addition, the assessment may include the amount of (e.g., signal obtained from, average signal obtained from, etc.) the ventricular cardiomyocyte specific binding member bound to the identified cells.

In certain embodiments, the method may include contacting the sample with an intracellular marker specific binding member. As cGMP has been shown to be dysregulated in an number of cardiac pathologies, the method may include contacting the sample with a cyclic GMP (cGMP) specific binding member or a binding member specific for a protein in the cGMP synthesis pathway, such as Phosphodiesterase 5A (PDE5A). In certain aspects, the intracellular marker specific binding member may be a myosin (e.g., MLC2A) specific binding member or a troponin (e.g., cTnI) specific binding member. Distinguishing may include providing an assessment of the amount of (e.g., signal obtained from, average signal obtained from, etc.) the intracellular marker specific binding member bound to an identified cardiomyocyte subset.

Distinguishing may include providing an assessment (e.g., to a user or operator of the method) based upon any of the above-mentioned characteristics of the identified cells. For example, the sample may be an aliquot from a cell culture, and distinguishing may include providing an assessment of whether the cell culture is suitable for use in a drug screen (e.g., such as when the number or relative number of the identified cells is above a predetermined threshold). In another example, the sample may be an aliquot from a cell culture, and distinguishing may include providing an assessment of whether the sample or cell culture is suitable for use in a cellular therapy (e.g., such as when the number or relative number of the identified cells is above a predetermined threshold, when an intracellular marker is highly expressed, etc.). The cellular therapy may be for a cardiac disease (i.e., heart disease, cardiovascular disease). For example, the cellular therapy may be administered to a subject after a heart attack, or to treat any other cardiac disease such as cardiomyopathy, heart failure, congenital heart disease, cardiac dysrhythmias, inflammatory heart disease, valvular heart disease, ventricular tachycardia or atrial fibrillation. In another example, the assessment may be a recommendation of whether a drug administered to cells of the sample is suitable for use in the treatment of a cardiac disease (e.g., any of the above mentioned cardiac diseases).

In some embodiments, the assessment may be provided by providing, i.e. generating, a written report that includes the artisan's assessment. Thus, a subject method may further include a step of generating or outputting a report providing the results of an assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to a subject assessment and its results. The report may include information about the testing facility, which information is relevant to the hospital, clinic, or laboratory in which sample gathering and/or data generation was conducted. Sample gathering can include obtaining a fluid sample, e.g. blood, saliva, urine etc.; a tissue sample, e.g. a tissue biopsy, etc. from a subject. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a patient data section, including patient medical history (which can include, e.g., age, race, serotype, etc.), as well as administrative patient data such as information to identify the patient (e.g., name, patient date of birth (DOB), gender, mailing and/or residence address, medical record number (MRN), room and/or bed number in a healthcare facility), insurance information, and the like), the name of the patient's physician or other health professional who ordered the monitoring assessment and, if different from the ordering physician, the name of a staff physician who is responsible for the patient's care (e.g., primary care physician).

The report may include a sample data section, which may provide information about the biological sample analyzed in the assessment, such as the source of biological sample obtained from the patient (e.g. blood, saliva, or type of tissue, etc.), how the sample was handled (e.g. storage temperature, preparatory protocols) and the date and time collected. Report fields with this information can generally be populated using data entered by the user, some of which may be provided as pre-scripted selections (e.g., using a drop-down menu). The report may include an assessment report section, which may include information generated after processing of the data as described herein. The assessment portion of the report can optionally also include a recommendation(s).

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, etc.

It will be readily appreciated that the report can include all or some of the elements above, with the proviso that the report generally includes at least the elements sufficient to provide the analysis requested by the user.

In certain aspects, one or more of the above steps (e.g., identifying, separating, assessing, etc.) may be performed by flow cytometry. Flow cytometry is a methodology using multi-parameter data for identifying and distinguishing between different particles, such as cells or beads, that vary from one another (e.g., in terms of label, size, granularity, etc.) in a fluid medium. In flow cytometrically analyzing the particles (e.g., the cells prepared as described above), a liquid medium including the particles is first introduced into the flow path of the flow cytometer. When in the flow path, the particles are passed substantially one at a time through one or more sensing regions, where each of the particles is exposed individually to a source of monochromatic light and measurements of light scatter parameters and/or fluorescent emissions as desired (e.g., two or more light scatter parameters and measurements of one or more fluorescent emissions) are separately recorded for each particle. The data recorded for each particle is analyzed in real time or stored in a data storage and analysis means, such as a computer, as desired.

More specifically, in a flow cytometer, the particles are passed, in suspension, substantially one at a time in a flow path through one or more sensing regions where in each region each particle is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed.

In series with a sensing region, a detector module that includes one or more detectors, e.g., light sensors, such as photomultiplier tubes (or "PMT"), is used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. The forward light scatter (or FSC), orthogonal light scatter (SSC), and each fluorescence emissions include a separate parameter for each particle (i.e. each "event"). Thus, for example, two, three four or more parameters can be collected (and recorded) from a particle labeled with two different fluorescence markers.

Flow cytometers further include data acquisition, analysis and recording means, such as a computer, wherein multiple data channels record data from each detector for the light scatter and fluorescence emitted by each particle as it passes through the sensing region. The purpose of the analysis system is to classify and count particles wherein each particle presents itself as a set of digitized parameter values. In flow cytometrically assaying particles in methods of the invention, the flow cytometer may be set to trigger on a selected parameter in order to distinguish the particles of interest from background and noise. "Trigger" refers to a preset threshold for detection of a parameter. It is typically used as a means for detecting passage of particle through the laser beam. Detection of an event that exceeds the preset threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for particle.

A particular subpopulation of interest may be further analyzed by "gating" (i.e. a type of threshold) based on the data collected for the entire sample. To select an appropriate gate, the data may be plotted (e.g., on a linear or logarithmic scale) so as to obtain the best separation of subpopulations possible. This procedure is typically done by plotting forward light scatter (FSC) vs. side (i.e., orthogonal) light scatter (SSC) on a two-dimensional dot plot. The flow cytometer operator then selects the desired subpopulation of particles (i.e., those cells within the gate) and excludes particles which are not within the gate. Where desired, the operator may select the gate by drawing a line around the desired subpopulation using a cursor on a computer screen. Only those particles within the gate are then further analyzed by plotting the other parameters for these particles, such as fluorescence. Gating based on fluorescence may then be used to further separate subpopulations of cells, as is seen in FIGS. 1 to 5.

Devices and Systems

Aspects of the invention further include systems for use in practicing embodiments of the subject methods. Systems of the invention may include a flow cytometer configured to assay particles (e.g., beads, cells, etc.) by measuring signals such as FSC, SSC, fluorescence emission maxima, light scatter, mass, molecular mass, etc. Aspects of the system include a flow channel, a detector module configured to obtain a signal from a detectably labeled ventricular cardiomyocyte specific binding member when present in an assay region of the flow channel, and a signal processing module configured to identify a cardiomyocyte subset based on a signal produced by the detectably labeled ventricular cardiomyocyte specific binding member. In certain aspects, the ventricular cardiomyocyte specific binding member may be a CD77 specific binding member. The flow channel may include a heterogeneous cellular sample that includes the ventricular cardiomyocyte specific binding member.

The signal processing module may be configured to perform any of the method steps of distinguishing (e.g., identifying, sorting, providing an assessment, etc.) such as described above. In certain embodiments, the signal processing module may be configured to identify a cell as belonging to a cardiomyocyte subset of interest (such as ventricular cardiomyocytes) when the intensity of the signal obtained from the cell is above a predetermined threshold. Alternatively or in addition, the signal processing module may be configured to identify a cell as belonging to the cardiomyocyte subset (such as atrial cardiomyocytes) when the intensity of the signal obtained from the cell is below a predetermined threshold.

In certain embodiments, the sample may further include a one or more non-cardiomyocyte specific binding members, and the cardiomyocyte subset may be identified based additionally on one or more signals provided by one or more non-cardiomyocyte specific binding members. The one or more non-cardiomyocyte specific binding members may be specific for one or more of CD90, CD140b, CD200, CD13, CD31, CD144, CD49a, CD167b and TRA-1-60. For example, the one or more non-cardiomyocyte specific binding members may be specific for one or more of CD90, CD140b and CD200. The sample may further include a detectably labeled cardiomyocyte specific binding member, and the cardiomyocyte subset may be identified based additionally on a signal provided by the non-cardiomyocyte specific binding member. The cardiomyocyte specific binding member may be specific for one of CD172a, CD340, CD43 and CD29. For example, the cardiomyocyte specific binding member may be specific for one of CD172a.

The signal processing module may be configured to separate the identified cardiomyocyte subset from other cells in the sample. Alternatively or in addition, the signal processing module may be configured to provide an assessment of the sample, e.g., based on the relative number of cells in the identified cardiomyocyte subset, the strength of the signal obtained from the identified cardiomyocyte subset, or a combination thereof. In certain aspects, the assessment may include a determination of whether a cell culture is suitable for use in a drug screen. Alternatively, the assessment may include a determination of whether the cell culture is suitable for use in a cellular therapy (e.g., for treatment of any of the heart diseases described herein).

In certain embodiments, the signal processing module may be configured to separate the identified cardiomyocyte subset from other cells in the sample. For example, the signal processing module may be configured to magnetically deflect a drop containing the identified cardiomyocyte subset toward a collection tube. The signal processing module may be configured to provide an assessment of whether a cell culture is suitable for use in a cellular therapy, based on the detected amount of the intracellular marker specific binding member bound to cells of the identified cardiomyocyte subset. Alternatively, the signal processing module may be configured to provide an assessment of whether a drug administered to cells of the sample is suitable for use in the treatment of a heart disease, based on the detected amount of the intracellular marker specific binding member bound to cells of the identified cardiomyocyte subset.

The system may be a flow cytometric system. Flow cytometers of interest include, but are not limited to, devices such as those described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference. The system may be configured to separate particles (e.g., cells or beads) into separate containers (e.g., one or more tubes, waste, etc.) based on a one or more light scatter and signals obtained from the particle.

The system can in certain embodiments include a computer that includes: a central processing unit; a main non-volatile storage drive, which can include one or more hard drives, for storing software and data, where the storage drive is controlled by disk controller; a system memory, e.g., high speed random-access memory (RAM), for storing system control programs, data, and application programs, including programs and data loaded from non-volatile storage drive; system memory can also include read-only memory (ROM); a user interface, including one or more input or output devices, such as a mouse, a keypad, and a display; an optional network interface card for connecting to any wired or wireless communication network, e.g., a printer; and an internal bus for interconnecting the aforementioned elements of the system.

Operation of computer is controlled primarily by operating system, which is executed by central processing unit. The operating system can be stored in a system memory. In some embodiments, the operating system may include a file system. In addition to an operating system, one possible implementation of the system memory includes a variety of programming files and data files for implementing the method described below. In certain cases, the programming can contain a program, where the program can be composed of various modules, and a user interface module that permits a user at user interface to manually select or change the inputs to or the parameters used by programming. The data files can include various inputs for the programming.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, flash drives, and solid state drives are all examples of permanent memory. Random Access Memory (RAM) is an example of non-permanent (i.e., volatile) memory. A file in permanent memory can be editable and re-writable.

In certain embodiments, instructions in accordance with any of the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a hard disk, optical disk, magneto-optical disk, CD-ROM, CD-R, non-volatile memory card, ROM, DVD-ROM, flash drive, solid state disk, and network attached storage (NAS), whether or not such devices are internal or external to the computer. A file containing information can be "stored" on computer readable medium, where "storing" means recording information such that it is accessible and retrievable at a later date by a computer.

Utility

The cell surface signatures described herein find use in distinguishing cardiomyocytes from other cells in heterogeneous cell culture. The cell surface signatures permit the identification, characterization and/or isolation of cardiomyocyte subsets of interest, such as atrial and ventricular cardiomyocytes.

The methods, systems and kits disclosed herein find use in isolating cardiomyocyte subsets from heterogeneous cell culture. For example, CD77 expression alone or in addition to any of a number of other cellular markers allows for ventricular or atrial cardiomyocyte separation and/or enrichment from multiple cell culture systems (e.g., primary isolation, monolayers, embryoid bodies of any suitable stem cell such as those discussed herein). The cardiomyocytes may be derived from a human patient's cells and may be useful in a cellular therapy of a cardiovascular disease. Additionally, the subject methods may be used to isolate a cardiomyocyte subset for use in screening drug (or small molecule) candidates. Cardiomyocyte subsets can be characterized (e.g., by looking at the number of cells, expression of CD77, or expression of additional markers such as cGMP) as a quality control prior to cell samples to be used in drug screens or cellular therapies, or to screen a cardiomyocyte subset after exposure to a drug.

Kits

In yet another aspect, the present invention provides kits for practicing the subject methods, e.g., as described above. The kit may include a ventricular cardiomyocyte specific binding member having a ventricular cardiomyocyte specific binding domain coupled to a first processing domain. The kit may further include a non-cardiomyocyte specific binding member having a non-cardiomyocyte specific binding domain coupled to a second processing domain (e.g., as described in the subject methods). Alternatively or in addition, the kit may include a cardiomyocyte specific binding member and/or an intracellular marker specific binding member (e.g., as described above in the subject methods). The processing domains each may include a solid support (such as a microparticle, magnetic microparticle, etc.) or a label domain as described in the subject methods.

In certain aspects, the kit may contain any suitable reagents for maintaining pluripotency and/or cell viability, such as fetal calf serum, human platelet lysate, and so forth. The kit may include differentiation reagents such as retinoic acid, fibroblast growth factor (FGF), activin A, bone morphogenic factor (BMP4), VEGF, Dickkopf-1 (DKK-1), exogenous glucose, leukemia inhibitory factor, ROS species, Verapamil, cyclosporine, 5-Aza-2'-deoxycytidine, ascorbic acid, or other factors suitable for inducing differentiation of stem cells (e.g., pluripotent stem cells), fibroblasts, or any other suitable precursor into cardiomyocytes (e.g., atrial and/or ventricular cardiomyocytes). In certain aspects the kit may contain a cell line, such as an embryonic stem cell line (e.g., in DMSO and frozen). The kit may further include a small molecule that modulates cardiomyocyte activity, such as nitric oxide (NO) or cyclic GMP (cGMP).

The kit may further include reagents for performing a flow cytometric assay. Examples of said reagents include buffers for at least one of reconstitution and dilution of the first and second detectible molecules, buffers for contacting a cell sample with one or both of the first and second detectible molecules, wash buffers, control cells, control beads, fluorescent beads for flow cytometer calibration and combinations thereof. In certain aspects, the kit may include one or more standardized controls. The standardized controls may be control particles such as control beads or control cells.

The specific binding members and/or reagents described above may be provided in liquid or dry (e.g., lyophilized) form. Any of the above components (detectible labels and/or reagents) may be present in separate containers (e.g., separate tubes, bottles, or wells in a multi-well strip or plate). In addition, one or more components may be combined into a single container, e.g., a glass or plastic vial, tube or bottle.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., a hard disk, optical disk, magneto-optical disk, CD-ROM, CD-R, non-volatile memory card, ROM, DVD-ROM, flash drive, solid state disk, etc., on which the information has been recorded. Yet another means that may be present is a website address which may be used via the internet to access the information at a removed site. Any convenient means may be present in the kits.

In addition, the kit may include any other components or reagents, of the above methods and systems.

The following examples are offered by way of illustration and not by way of limitation.

EXPERIMENTAL

An H9 cell line (a human embryonic stem cell line) expressing green fluorescent protein (GFP) under the Myosin Light Chain 2V (MLC2V) promoter, which is active in ventricular cardiomyocytes, was used in the following experiments. Differentiation of the H9 cell line was performed as discussed below. Cells were stained with antibody panels and analyzed by flow cytometry. $CD77^{bright}$ cells were observed to express GFP, while the subset of $CD172^{pos}$ cells that lacked high CD77 expression did not express high levels of GFP on average.

Example 1

Methods

H9 cells expressing GFP under the MLC2V promoter were cultured to form embryoid bodies. On day 24, cells were harvested and a surface stain was performed using various antibody panels as discussed in FIGS. 1 to 4 below.

Results

In FIG. 1 we identify a population of cells that is $CD77^{bright}$ $CD200^{neg}$ which is primarily GFP+, identifying the population as ventricular cardiomyocytes. Cells were stained with a CD200 specific antibody conjugated to PE Cy7 and a CD77 specific antibody conjugated to BV510. GFP expression was measured using the FITC channel. Live cells (P1) were gated by forward scatter and side scatter as shown in FIG. 1A. GFP+ cells were gated based on fluorescence in the FITC and APC channels, as shown in FIG. 1B (gate P2). As shown in FIG. 1C, GFP+ cells are $CD77^{bright}$ and $CD200^{neg}$. $CD77^{bright}$ $CD200^{neg}$ cells were gated as shown in FIG. 1D (gate P3). As shown in FIG. 1E, $CD77^{bright}$ $CD200^{neg}$ cells are GFP+.

Figure 2:
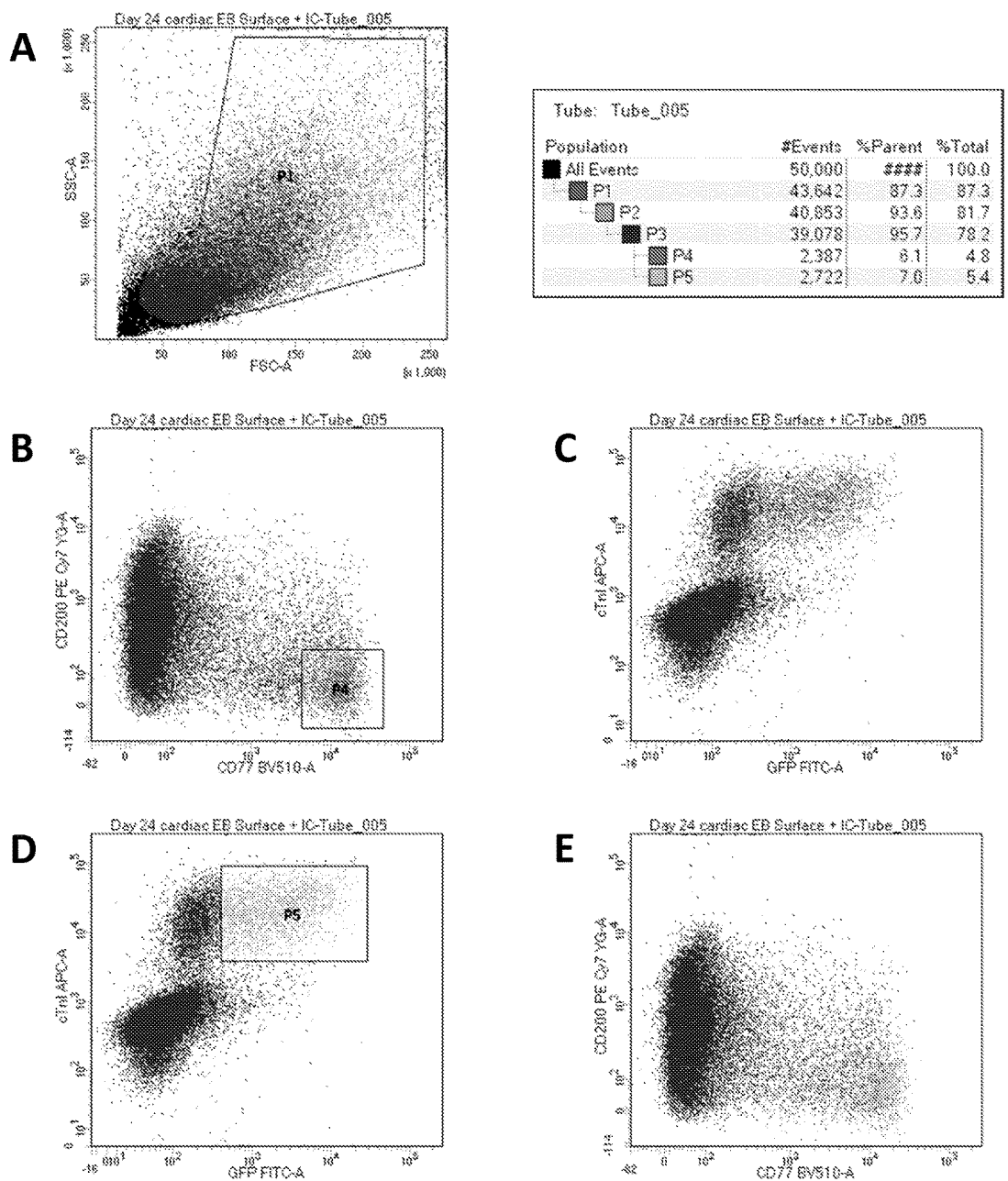
FIGS. 2A-E provide scatter plots showing further gating and analysis of the cells of FIG. 1.

In FIG. 2 we confirm that the GFP+ cells express cTnI, further characterizing the $CD77^{high}$ $CD200^{neg}$ population as ventricular cardiomyocytes. Cells were further stained with cTnI antibody conjugated to APC in addition to the staining panel described in FIG. 1. $CD77^{bright}$ $CD200^{neg}$ cells were gated as shown in FIG. 2B (gate P4), and displayed high expression of GFP and cTnI as shown in FIG. 2C. GFP+ and $cTnI^{high}$ cells were gated as shown in FIG. 2D (gate P5), and displayed high expression of CD77 as shown in FIG. 2E.

Figure 3A:
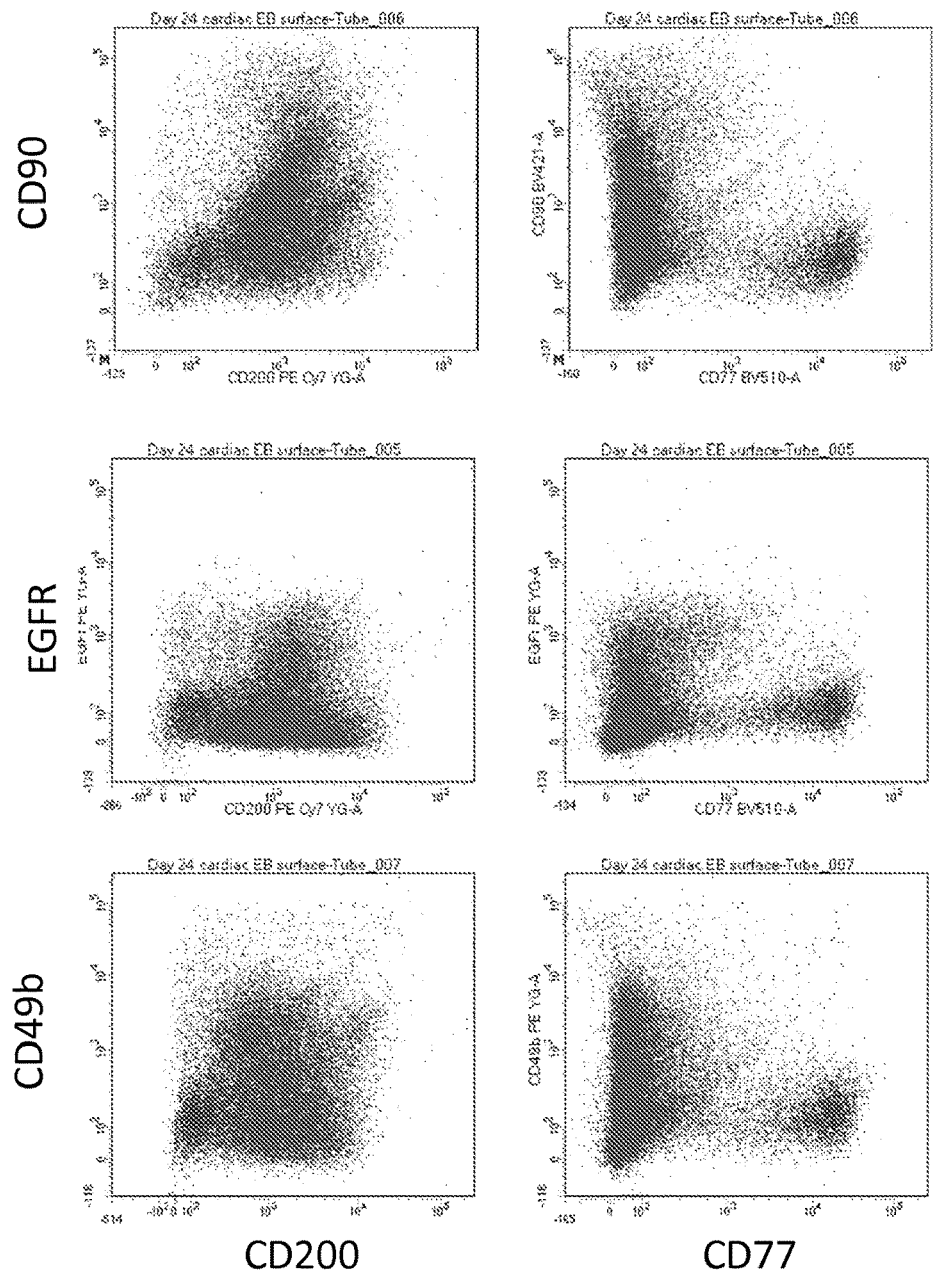
FIGS. 3A-B provide scatter plots of the cell line of FIG. 1 after 25 days of embryoid body culture, showing expression of CD200 (left column) and of CD77 (right column) with: CD90, EGFR and CD49b (FIG. 3A) and CD140b, CD49a and CD141 (FIG. 3B). GFP+ cell events, gated as shown in FIG. 1B, are colored green.
Figure 3B:
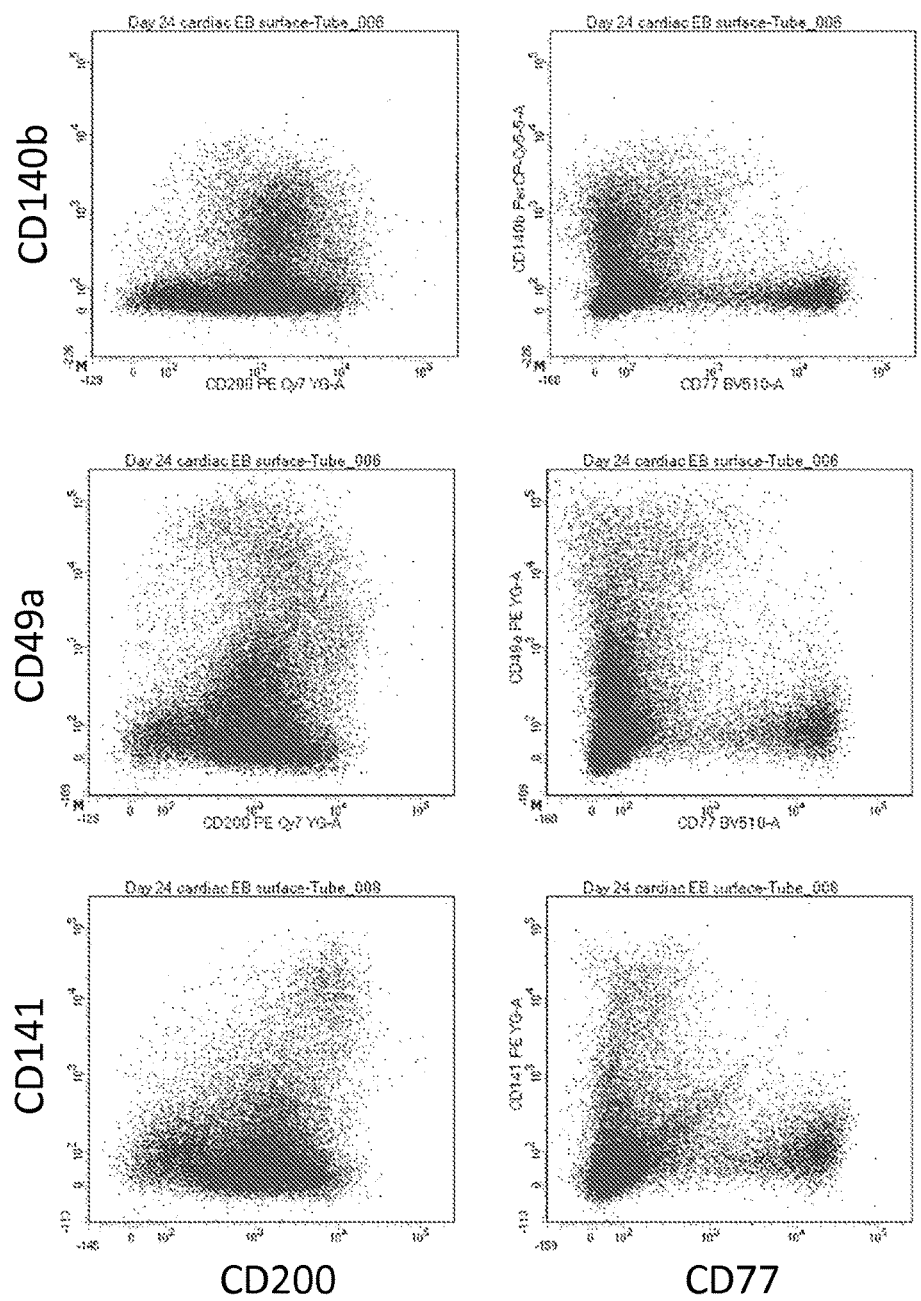

In FIG. 3 we utilize a number of staining panels to identify a number of cellular markers that are expressed at low levels in the GFP+ cell population. FIG. 3A shows expression of CD90 (top), EGFR (middle) and CD49b (bottom) with CD200 (left side) and CD77 (right side). Green cell events are GFP+ cells gated as shown in FIG. 1B. FIG. 3B shows expression of CD140b (top), CD49a (middle) and CD141 (bottom) with CD200 (left side) and CD77 (right side). Green cell events are GFP+ cells gated as shown in FIG. 1B. All cellular markers other than CD77 are lowly expressed in the GPF+ cell population.

Figure 4A:
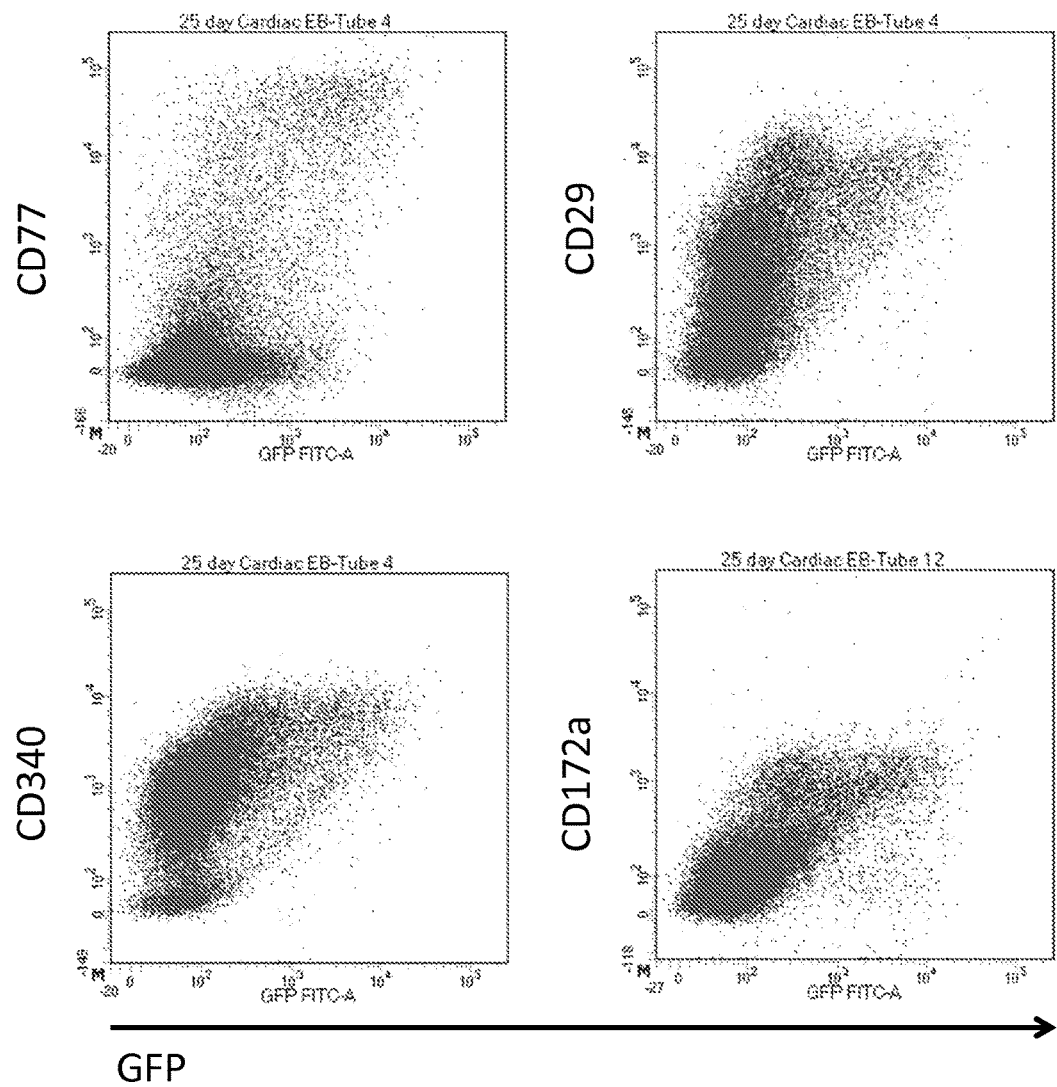
FIGS. 4A-B provide scatter plots of the cell line of FIG. 1 after 25 days of embryoid body culture.
Figure 4B:
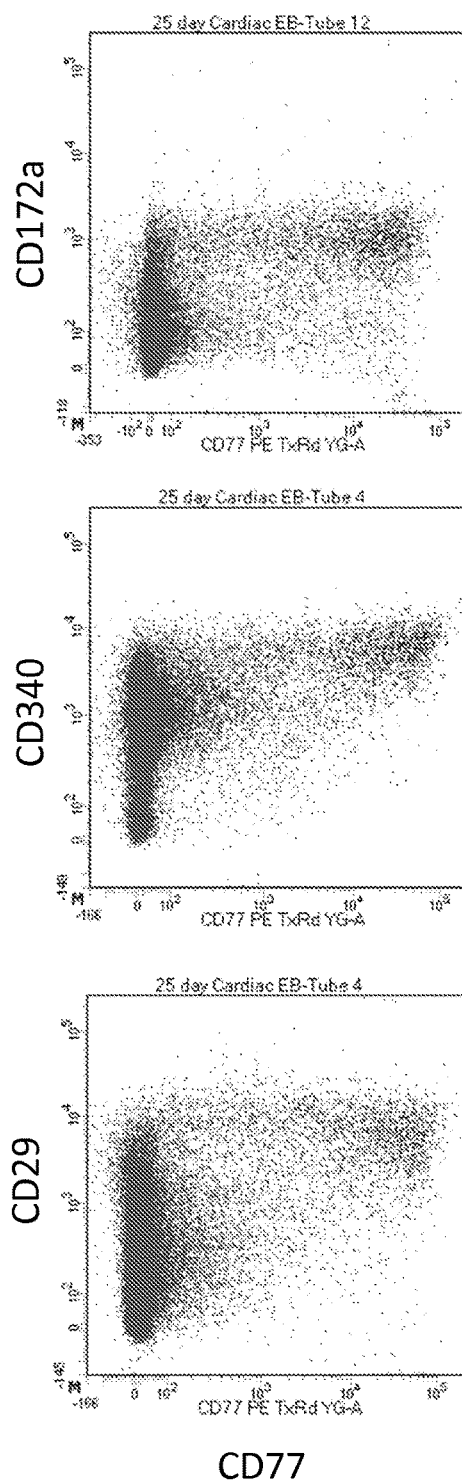

In FIG. 4 we look at co-expression of CD77, CD29, CD340, and CD172a and how they co-express with GFP (FIG. 4A), and co-expression of CD29, CD340, and CD172a with CD77 (FIG. 4B). We also identify the ventricular cardiomyocytes as the GFP+ population. Here we see that the GFP+ cells are co-expressed with the above markers (CD77, CD29, CD340, and CD172a), any of which can be utilized as positive markers for sorting ventricular cardiomyocytes.

Example 2

Methods

H9 cells expressing GFP under the MLC2V promoter were cultured as a monolayer. On day 20, cells were harvested and a surface stain was performed as discussed in FIG. 5 below.

Results

Figure 5A:
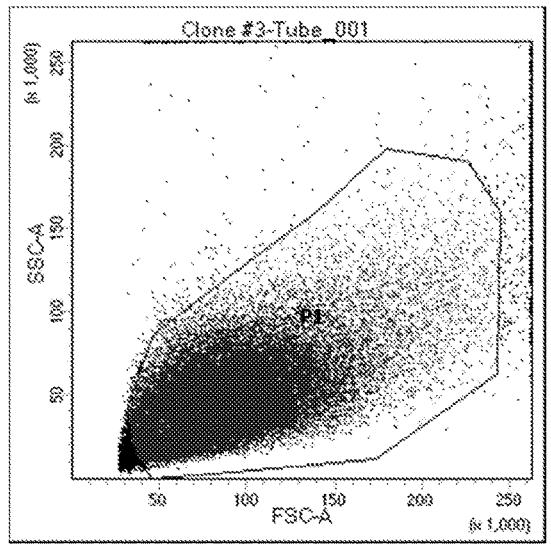
FIGS. 5A-B provide scatter plots of the cell line of FIG. 1 after 20 days of cell culture as a monolayer.
Figure 5A:
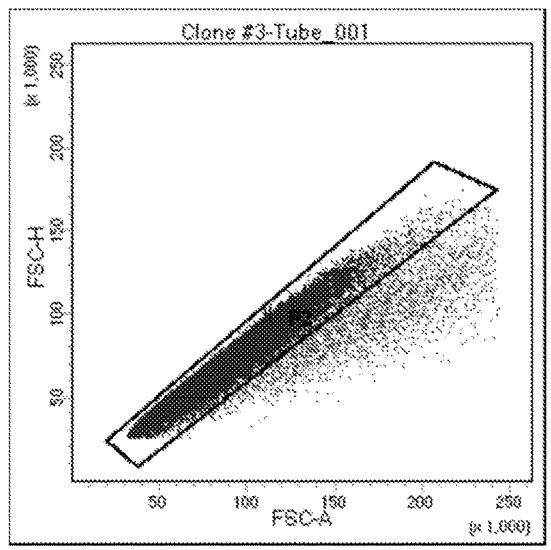
Figure 5B:
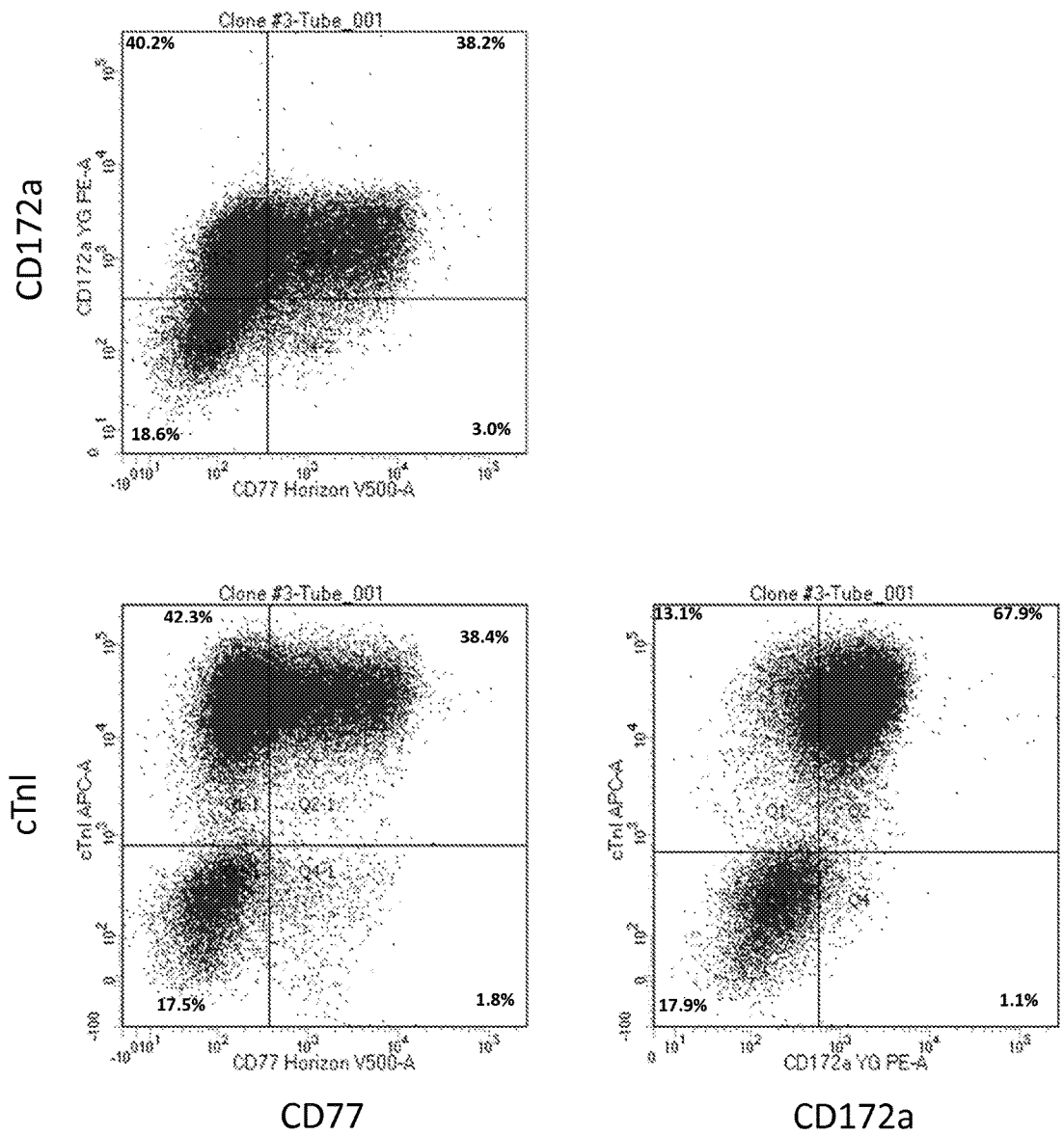

In FIG. 5 we show that that all the majority of $CD172a^+$ cells co-express cTnI. A subset of CD172a also express CD77, which we identified as ventricular cardiomyoctes. In addition, there is a population of cells that are $CD172a^{pos}CD77^{neg}$. These may be atrial cardiomyocytes or a common progenitor that are not mature enough to express cTnI.

Notwithstanding the appended clauses, the disclosure set forth herein is also defined by the following clauses:

1. A method of distinguishing a cardiomyocyte subset in a heterogeneous cellular sample, the method comprising:
   contacting the heterogeneous cellular sample with a cell surface marker specific binding member(s); and
   distinguishing the cardiomyocyte subset based on whether the cell surface marker specific binding member(s) binds to constituents of the sample.
2. The method of Clause 1, wherein the cardiomyocyte subset comprises ventricular cardiomyocytes.
3. The method of Clause 1, wherein the cardiomyocyte subset comprises atrial cardiomyocytes.
4. The method according to any of Clauses 1 to 3, wherein the cell surface marker specific binding member is a ventricular cardiomyocyte cell surface specific binding member.
5. The method according to Clause 4, wherein the ventricular cardiomyocyte cell surface specific binding member is a CD77 specific binding member.
6. The method according to Clause 4 or 5, further comprising contacting the sample with one or more non-cardiomyocyte cell surface specific binding members.
7. The method according to Clause 6, wherein the one or more non-cardiomyocyte cell surface specific binding members are selected from the group consisting of specific binding members for CD90, CD140b, CD200, CD13, CD31, CD144, CD49a, CD167b or TRA-1-60.
8. The method according to Clause 7, wherein the one or more non-cardiomyocyte specific binding members are selected from the group consisting of specific binding members for CD90, CD140b, and CD200.

9. The method according to any of Clauses 6 to 8, further comprising contacting the sample with a cardiomyocyte cell surface specific binding member.
10. The method according to Clause 9, wherein the cardiomyocyte cell surface specific binding member is selected from the group consisting of specific binding members for CD172a, CD340, CD43 and CD29.
11. The method according to Clause 10, wherein the cardiomyocyte cell surface specific binding member is specific for CD172a.
12. The method according to any of Clauses 1 to 3, wherein the cell surface marker specific binding member is a non-cardiomyocyte cell surface specific binding member.
13. The method according to Clause 12, wherein the non-cardiomyocyte cell surface specific binding member is selected from the group consisting of specific binding members for CD90, CD140b, CD13, CD31, CD144, CD49a, CD167b, and TRA-1-60.
14. The method of any of Clauses 1 to 13, wherein distinguishing comprises at least one of separating, enriching, identifying and providing an assessment.
15. The method according to Clause 14, wherein the distinguishing comprises separating cells bound to the cell surface marker specific binding member.
16. The method according to Clause 15, wherein the separated cells comprise ventricular cardiomyocytes.
17. The method according to Clause 15, wherein the separated cells comprises atrial cardiomyocytes.
18. The method according to any of Clause 14, wherein distinguishing comprises enriching for the cardiomyocyte subset by depleting cells bound to the surface marker specific binding member.
19. The method according to any of Clauses 18, wherein one or more of the specific binding members are conjugated to a solid support.
20. The method according to Clause 19, wherein the solid support comprises a microparticle.
21. The method according to Clause 20, wherein the microparticle comprises a magnetic microparticle.
22. The method according to Clause 21, wherein the method comprises applying a magnetic field to the specific binding member contacted cellular sample.
23. The method according to Clause 14, wherein the distinguishing comprises identifying a cardiomyocyte subset in the heterogeneous cellular sample.
24. The method according to Clause 23, wherein the cardiomyocyte subset comprises ventricular cardiomyocytes.
25. The method according to Clause 24, wherein the cardiomyocyte subset is identified as comprising ventricular cardiomyocytes when a signal obtained from the sample exceeds a predetermined threshold value.
26. The method according to Clause 23, wherein the cardiomyocyte subset comprises atrial cardiomyocytes.
27. The method according to Clause 26, wherein the cardiomyocyte subset is identified as comprising atrial cardiomyocytes when a signal obtained from the sample exceeds a predetermined threshold value.
28. The method according to Clause 14, wherein the distinguishing comprises providing an assessment of the cardiomyocyte subset.
29. The method according to Clause 28, wherein the assessment comprises relative number of identified cells.
30. The method according to any of the preceding clauses, wherein the method further comprises contacting the sample with an intracellular marker specific binding member.
31. The method according to Clause 30 wherein the intracellular marker specific binding member is a cGMP specific binding member.
32. The method according to Clause 30 or 31, wherein the method further comprises providing an assessment of the amount of the intracellular marker specific binding member bound to the identified cells.
33. The method according to Clause 32, wherein the amount is an average amount.
34. The method according to any of the preceding clauses, wherein the sample is an aliquot from a cell culture.
35. The method according to Clause 34, wherein the method comprises providing an assessment of whether the cell culture is suitable for use in a drug screen.
36. The method according to Clause 35, wherein the method further comprises providing an assessment of whether a drug administered to cells of the sample is suitable for use in the treatment of a cardiac disease.
37. The method according to Clause 34, wherein the method further comprises providing an assessment of whether the cell culture is suitable for use in a cellular therapy.
38. The method according to any of Clauses 1 to 37, wherein one or more of the specific binding members comprises an antibody or a fragment thereof.
39. The method according to any of Clauses 1 to 38, wherein one or more of the specific binding members comprise a label domain.
40. The method according to Clause 39, wherein the label domain comprises a fluorescent label.
41. The method according to Clause 40, wherein the distinguishing comprises flow cytometry.
42. The method according to any of Clauses 1 to 41, wherein the sample comprises live cells.
43. A heterogeneous cellular sample comprising:
    live cardiomyocytes; and
    a ventricular cardiomyocyte specific binding member.
44. The sample according to Clause 43, wherein the ventricular cardiomyocyte specific binding member is a CD77 specific binding member.
45. The sample according to Clause 43 or 44, further comprising one or more non-cardiomyocyte specific binding members.
46. The sample according to Clause 45, wherein the one or more non-cardiomyocyte specific binding members are selected from the group consisting of binding members for CD90, CD140b, CD200, CD13, CD31, CD144, CD49a, CD167b, and TRA-1-60.
47. The sample according to Clause 46, wherein the one or more non-cardiomyocyte specific binding members are selected from the group consisting of specific binding members for CD90, CD140b, and CD200.
48. The sample according to any of Clauses 45 to 47, further comprising a cardiomyocyte specific binding member.
49. The sample according to Clause 48, wherein the cardiomyocyte specific binding member is selected from the group consisting of specific binding members for CD172a, CD340, CD43 and CD29.
50. The sample according to Clause 49, wherein the cardiomyocyte specific binding member is specific for CD172a.
51. The sample according to any of Clauses 43 to 50, wherein one or more of the specific binding members comprises an antibody or a binding fragment thereof.
52. The sample according to any of Clauses 43 to 51, wherein one or more of the specific binding members comprises a label domain.
53. The sample according to Clause 52, wherein the label domain is a fluorescent label.

54. The sample according to Clause 53, wherein one or more of the specific binding members is conjugated to a solid support.
55. The sample according to Clause 54, wherein the solid support comprises a microparticle.
56. The sample according to Clause 55, wherein the microparticle comprises a magnetic microparticle.
57. The sample according to any of Clauses 43 to 56, wherein the cardiomyocytes comprise ventricular cardiomyocytes.
58. The sample according to any of Clauses 43 to 56, wherein the cardiomyocytes comprise atrial cardiomyocytes.
59. The sample according to any of Clauses 43 to 58, further comprising induced pluripotent stem cells.
60. The sample according to any of Clauses 43 to 59, further comprising embryonic stem cells.
61. The sample according to any of Clauses 43 to 60, further comprising feeder cells.
62. The sample according to any of Clauses 43 to 61, wherein the sample is a neural differentiation culture of hPSCs.
63. The sample according to any of Clauses 43 to 62, wherein the sample is an induced cardiac culture from fibroblasts.
64. The sample according to any of Clauses 43 to 63, wherein the cells in the sample are mammalian cells.
65. The sample according to Clause 64, wherein the mammalian cells are human cells.
66. A system comprising:
a flow channel;
a detector module configured to obtain a signal from a detectably labeled ventricular cardiomyocyte specific binding member when present in an assay region of the flow channel; and
a signal processing module configured to identify a cardiomyocyte subset based on a signal produced by the detectably labeled ventricular cardiomyocyte specific binding member.
67. The system of Clause 66, wherein the ventricular cardiomyocyte specific binding member is a CD77 specific binding member.
68. The system according to any of Clauses 66 to 67, wherein the flow channel comprises a heterogeneous cellular sample.
69. The system according to Clause 68, wherein the heterogeneous cellular sample comprises a detectably labeled ventricular cardiomyocyte specific binding member.
70. The system according to Clause 69, wherein the signal processing module is configured to identify a cell as belonging to the cardiomyocyte subset when the intensity of the signal obtained from the cell is above a predetermined threshold.
71. The system according to Clause 70, wherein the cardiomyocyte subset comprises ventricular cardiomyocytes.
72. The system according to Clause 69, wherein the signal processing module is configured to identify a cell as belonging to the cardiomyocyte subset when the intensity of the signal obtained from the cell is below a predetermined threshold.
73. The system according to Clause 72, wherein the cardiomyocyte subset comprises atrial cardiomyocytes.
74. The system according to any of Clauses 69 to 73, wherein the signal processing module is further configured to separate the identified cardiomyocyte subset from other cells in the sample.
75. The system according to any of Clauses 69 to 74, wherein the signal processing module is further configured to provide an assessment of the sample, based on the total number of cells in the identified cardiomyocyte subset.
76. The system according to any of Clauses 69 to 75, wherein the signal processing module is further configured to provide an assessment of the sample, based on the relative number of cells in the identified cardiomyocyte subset.
77. The system according to any of Clauses 69 to 74, wherein the signal processing module is further configured to provide an assessment of the sample, based on the strength of the signal obtained from cells in the identified cardiomyocyte subset.
78. The system according to any of Clauses 75 to 77, wherein the assessment is a determination of whether a cell culture is suitable for use in a drug screen.
79. The system according to any of Clauses 75 to 77, wherein the assessment is a determination of whether a cell culture is suitable for use in a cellular therapy.
80. The system according to Clause 69, wherein the sample further comprises a detectably labeled intracellular marker specific binding member.
81. The system according to Clause 80, wherein the intracellular marker specific binding member is a cGMP specific binding member.
82. The system according to Clause 80 or 81, wherein the signal processing module is further configured to provide an assessment of whether a cell culture is suitable for use in a cellular therapy, based on the detected amount of the intracellular marker specific binding member bound to cells of the identified cardiomyocyte subset.
83. The system according to Clause 80 or 81, wherein the signal processing module is further configured to provide an assessment of whether a drug administered to cells of the sample is suitable for use in the treatment of a heart disease, based on the detected amount of the intracellular marker specific binding member bound to cells of the identified cardiomyocyte subset.
84. The system according to any of Clauses 69 to 83, wherein the sample further comprises one or more detectably labeled non-cardiomyocyte specific binding members, and wherein the cardiomyocyte subset is further identified based on one or more signals provided by the one or more non-cardiomyocyte specific binding member.
85. The system according to Clause 84, wherein the one or more non-cardiomyocyte specific binding members are selected from the group consisting of specific binding members for one of CD90, CD140b, CD200, CD13, CD31, CD144, CD49a, CD167b, and TRA-1-60.
86. The system according to Clause 85, wherein the one or more non-cardiomyocyte specific binding members are selected from the group consisting of specific binding members for CD90, CD140b, and CD200.
87. The system according to any of Clauses 69 to 86, wherein the sample further comprises a detectably labeled cardiomyocyte specific binding member, and wherein the cardiomyocyte subset is further identified based on one or more signals provided by the one or more non-cardiomyocyte specific binding member.
88. The system according to 87, wherein the cardiomyocyte specific binding member is selected from the group consisting of binding members specific for CD172a, CD340, CD43 and CD29.
89. The system according to Clause 88, wherein the cardiomyocyte specific binding member is specific for CD172a.

90. The system according to any of Clauses 66 to 89, wherein the system is a flow cytometric system.

91. A kit comprising:
a ventricular cardiomyocyte specific binding member comprising a ventricular cardiomyocyte specific binding domain coupled to a first processing domain; and
a non-cardiomyocyte specific binding member comprising a non-cardiomyocyte specific binding domain coupled to a second processing domain.

92. The kit of Clause 91, wherein the ventricular cardiomyocyte specific binding member comprises a CD77 specific binding member.

93. The kit according to Clause 91 or 92, wherein the one or more non-cardiomyocyte specific binding members are selected from the group consisting of specific binding members for CD90, CD140b, CD200, CD13, CD31, CD144, CD49a, CD167b, and TRA-1-60.

94. The kit according to Clause 93, wherein the kit comprises multiple non-cardiomyocyte specific binding members, and wherein the multiple non-cardiomyocyte specific binding members are specific for CD90, CD140b, and CD200.

95. The kit according to any of Clauses 91 to 94, wherein at least one of the first and second processing domains comprise a solid support.

96. The kit according to Clause 95, wherein the solid support comprises a microparticle.

97. The kit according to Clause 96, wherein the microparticle comprises a magnetic microparticle.

98. The kit according to any of Clauses 91 to 97, wherein at least one of the first and second processing domains comprises a detectable label.

99. The kit according to Clause 98, wherein the detectable label comprises a fluorescent label.

100. The kit according to any of Clauses 91 to 99, wherein at least one of the ventricular cardiomyocyte specific binding domain and the non-cardiomyocyte specific binding domain is an antibody or a binding fragment thereof.

101. The kit according to any of Clauses 91 to 100, further comprising a cardiomyocyte specific binding member.

102. The kit according to Clause 101, wherein the cardiomyocyte specific binding member is selected from the group consisting of specific binding members for CD172a, CD340, CD43 and CD29.

103. The kit according to Clause 102, wherein the cardiomyocyte specific binding member is specific for CD172a.

104. The kit according to any of Clauses 91 to 103, further comprising an intracellular marker specific binding member.

105. The kit according to Clause 104, wherein the intracellular marker specific binding member comprises a cGMP specific binding member.

106. The kit according to any of Clauses 91 to 105, wherein the specific binding members are provided in separate containers.

107. The kit according to any of Clauses 91 to 105, wherein the specific binding members are provided in the same container.

108. The kit according to any of Clauses 107, further comprising differentiation reagents.

109. The kit according to Clause 108, wherein the differentiation reagents induce differentiation of stem cells into cardiomyocytes.

110. The kit according to Clause 109, wherein the differentiation reagents induce differentiation of fibroblasts into cardiomyocytes.

111. The kit according to any of Clauses 91 to 110, further comprising a small molecule that modulates cardiomyocyte activity.

112. The kit according to Clause 111, wherein the small molecule is cGMP.

113. The kit according to any of Clauses 91 to 112, further comprising reagents for performing flow cytometry.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of distinguishing a ventricular cardiomyocyte subset in a heterogeneous cellular sample, the method comprising:
contacting the heterogeneous cellular sample comprising ventricular cardiomyocytes, atrial cardiomyocytes, and non-cardiomyocytes with a ventricular cardiomyocyte cell surface marker specific binding member wherein the ventricular cardiomyocyte cell surface marker specific binding member is a CD77 specific binding member; and
distinguishing the ventricular cardiomyocyte subset based on whether the ventricular cardiomyocyte cell surface marker specific binding member binds to a cell surface marker on ventricular cardiomyocytes of the sample.

2. The method according to claim 1, further comprising contacting the sample with one or more non-cardiomyocyte cell surface specific binding members.

3. The method according to claim 2, wherein the one or more non-cardiomyocyte cell surface specific binding members are selected from the group consisting of specific binding members for CD90, CD140b, CD200, CD13, CD31, CD144, CD49a, CD167b and TRA-1-60.

4. The method according to claim 1, further comprising contacting the sample with a cardiomyocyte cell surface specific binding member.

5. The method according to claim 4, wherein the cardiomyocyte cell surface specific binding member is selected from the group consisting of specific binding members for CD172a, CD340, CD43 and CD29.

6. The method according to claim 1, wherein the cell surface marker specific binding member is a non-cardiomyocyte cell surface specific binding member.

7. The method according to claim 6, wherein the non-cardiomyocyte cell surface specific binding member is selected from the group consisting of specific binding members for CD90, CD140b, CD13, CD31, CD144, CD49a, CD167b, and TRA-1-60.

8. The method according to claim 1, wherein distinguishing comprises at least one of separating, enriching, identifying and providing an assessment.

9. The method according to claim 1, wherein one or more of the specific binding members comprises an antibody or a fragment thereof.

10. The method according to claim 1, wherein the distinguishing comprises flow cytometry.

11. The method according to claim 1, wherein the heterogeneous cell sample comprises cardiomyocyte precursors.

12. A composition comprising:
a heterogeneous cellular sample comprising live cardiomyocytes; and
a ventricular cardiomyocyte cell surface marker specific binding member, wherein the ventricular cardiomyocyte cell surface marker specific binding member is a CD77 specific binding member.

13. A kit comprising:
a ventricular cardiomyocyte cell surface marker specific binding member comprising a ventricular cardiomyocyte specific binding domain coupled to a first processing domain wherein the ventricular cardiomyocyte cell surface marker specific binding member is a CD77 specific binding member; and
a non-cardiomyocyte specific binding member comprising a non-cardiomyocyte specific binding domain coupled to a second processing domain.

* * * * *